US008050751B2

(12) United States Patent
Zhang et al.

(10) Patent No.: US 8,050,751 B2
(45) Date of Patent: Nov. 1, 2011

(54) PERIODIC BEAT DETECTION TO DETECT ARTIFACTS IN A CARDIAC ELECTROGRAM

(75) Inventors: Xusheng Zhang, Shoreview, MN (US); Raja N. Ghanem, Edina, MN (US); Robert W. Stadler, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 564 days.

(21) Appl. No.: 12/183,950

(22) Filed: Jul. 31, 2008

(65) Prior Publication Data
US 2010/0030093 A1    Feb. 4, 2010

(51) Int. Cl.
*A61B 5/0464*    (2006.01)
(52) U.S. Cl. ............. 600/518; 607/26; 607/27; 607/28; 600/508; 600/509; 600/517; 600/519
(58) Field of Classification Search ............... 607/26–28; 600/508–528
See application file for complete search history.

(56) References Cited

U.S. PATENT DOCUMENTS

| | | | |
|---|---|---|---|
| 3,552,386 A | | 1/1971 | Horth |
| 3,878,833 A | | 4/1975 | Arneson et al. |
| 4,027,657 A | | 6/1977 | Sureau et al. |
| 4,342,318 A | | 8/1982 | Engle et al. |
| 4,374,382 A | | 2/1983 | Markowitz |
| 4,411,271 A | | 10/1983 | Markowitz |
| 4,457,315 A | * | 7/1984 | Bennish ......................... 600/517 |
| 4,617,938 A | | 10/1986 | Shimoni et al. |
| 4,919,144 A | | 4/1990 | Vandehey |
| 5,107,849 A | | 4/1992 | Bellin et al. |
| 5,117,824 A | | 6/1992 | Keimel et al. |
| 5,431,693 A | * | 7/1995 | Schroeppel ...................... 607/28 |

(Continued)

FOREIGN PATENT DOCUMENTS
WO    WO 83/04171 A1    12/1983

OTHER PUBLICATIONS

Dan Sapoznikov et al., "Computer processing of artifact and arrhythmias in heart rate variability analysis," *Computer Methods and Programs in Biomedicine*, vol. 39 (1992) pp. 75-84.

(Continued)

*Primary Examiner* — Niketa Patel
*Assistant Examiner* — Rex R Holmes
(74) *Attorney, Agent, or Firm* — Michael C. Soldner (57) ABSTRACT

Techniques for determining whether artifacts are present in a cardiac electrogram are described. According to one example, a medical device senses a cardiac electrogram via electrodes. The medical device determines a derivative, e.g., a second order derivative, the electrogram. The medical device detects beats within the derivative, e.g., by comparing a rectified version of the derivative to one or more thresholds determined based on a maximum of the rectified derivative. The medical device determines whether the beats are periodic, and determines whether artifacts are present in the cardiac electrogram based on the determination of whether the beats are periodic. The medical device may further determine whether tachyarrhythmia is present and/or whether the cardiac rhythm of the patient is treatable based on the determination of whether the beats are periodic. For example, the medical device may determine that an electrogram is not treatable when the beats are periodic.

30 Claims, 9 Drawing Sheets

U.S. PATENT DOCUMENTS

| | | | |
|---|---|---|---|
| 5,545,186 | A | 8/1996 | Olson et al. |
| 5,749,900 | A | 5/1998 | Schroeppel et al. |
| 5,755,736 | A | 5/1998 | Gillberg et al. |
| 6,035,233 | A | 3/2000 | Schroeppel et al. |
| 6,571,121 | B2 | 5/2003 | Schroeppel et al. |
| 6,571,122 | B2 | 5/2003 | Schroeppel et al. |
| 6,675,042 | B2 | 1/2004 | Swerdlow et al. |
| 6,922,584 | B2 | 7/2005 | Wang et al. |
| 7,027,858 | B2 | 4/2006 | Cao et al. |
| 7,039,457 | B2 | 5/2006 | Young et al. |
| 7,257,441 | B2 | 8/2007 | Swerdlow et al. |
| 7,272,432 | B2 | 9/2007 | Kaiser et al. |
| 7,336,995 | B2 | 2/2008 | Armoundas et al. |
| 2006/0235476 | A1 | 10/2006 | Gunderson et al. |
| 2007/0239049 | A1* | 10/2007 | Ghanem et al. ............... 600/512 |
| 2008/0033494 | A1 | 2/2008 | Swerdlow |

OTHER PUBLICATIONS

Jeromie Rand et al., "Real-Time Correction of Heart Interbeat Intervals," IEEE Transactions on Biomedical Engineering, vol. 54, No. 5, May 1997, pp. 946-950.

Gary M. Friesen et al., "A Comparison of the Noise Sensitivity of Nine QRS Detection Algorithms," IEEE Transactions on Biomedical Engineering, vol. 37 (Jan. 1990), No. 1, pp. 85-98.

International Search Report and Written Opinion from corresponding PCT Application Serial No. PCT/US2008/009244 mailed Mar. 11, 2009 (12 pages).

International Preliminary Report on Patentability from corresponding PCT Application Serial No. PCT/US2008/009244 dated Jul. 12, 2010 (6 pages).

Reply to Written Opinion from corresponding PCT Application Serial No. PCT/US2008/009244 filed Jun. 19, 2009 (6 pages).

* cited by examiner

PERIODIC BEAT DETECTION TO DETECT ARTIFACTS IN A CARDIAC ELECTROGRAM

TECHNICAL FIELD

This disclosure relates to medical devices and, more particularly, to medical devices that monitor cardiac signals.

BACKGROUND

A variety of implantable medical devices for delivering a therapy and/or monitoring a physiological condition have been clinically implanted or proposed for clinical implantation in patients. Implantable medical devices may deliver electrical stimulation or fluid therapy and/or monitor conditions associated with the heart, muscle, nerve, brain, stomach or other organs or tissue. Some implantable medical devices include electrodes, and/or are coupled to electrodes via one or more implantable medical leads, for sensing intrinsic electrical signals within the patient and/or delivering electrical stimulation therapy to the patient.

Implantable medical devices, such as cardiac pacemakers or implantable cardioverter-defibrillators, for example, provide therapeutic electrical stimulation to the heart via implanted electrodes. The electrical stimulation may include signals such as pulses or shocks for pacing, cardioversion or defibrillation. In some cases, an implantable medical device may sense intrinsic depolarizations of the heart, and control delivery of stimulation signals to the heart based on the sensed depolarizations. Upon detection of an abnormal rhythm, such as bradycardia, tachycardia or fibrillation, an appropriate electrical stimulation signal or signals may be delivered to restore or maintain a more normal rhythm. For example, in some cases, an implantable medical device may deliver pacing pulses to the heart of the patient upon detecting tachycardia or bradycardia, and deliver cardioversion or defibrillation shocks to the heart upon detecting tachycardia or fibrillation.

Implantable pacemakers, cardioverters, defibrillators, or pacemaker-cardioverter-defibrillators are typically coupled to one or more intracardiac leads that carry electrodes for cardiac sensing and delivery of therapeutic stimulation. Subcutaneous devices, e.g., loop-recorders, which typically are not coupled to leads, have been used to monitor cardiac signals. Subcutaneously implantable medical devices may include a plurality of electrodes on or integrated with the housing of the device.

Additionally, subcutaneous devices and have been proposed for use in detecting of tachyarrhythmias and delivering responsive shocks. Such proposals have typically involved coupling a subcutaneously implanted medical device to one or more subcutaneously implanted electrodes via one or more implantable leads, although leadless, subcutaneous cardioverters of defibrillators have been proposed. Cardiac sensing and delivery of therapeutic shocks in such systems may be between a plurality of electrodes on the device housing, between an electrode on the device housing and a lead-borne electrode, or between lead-borne electrodes. It has also been proposed to deliver cardiac pacing pulses using such devices.

A cardiac signal sensed by an implantable medical device may include artifacts. In some cases, an implantable medical device may mistake an artifact for a cardiac depolarization. In some cases, the rate and duration of such artifacts may be such that an implantable medical device may interpret the artifacts to be a tachyarrhythmia.

Examples of an artifact that may be present in a sensed cardiac signal include motion artifacts, electromagnetic interference, or artifacts due to continuity or integrity issues with leads. Patient motion artifacts may be particularly evident in signals sensed via subcutaneous electrodes due to electromyographic signals generated by adjacent muscle groups within the patient. Limb and trunk movements or even breathing can generate noise spikes that are superimposed upon cardiac signal, and can make it appear to reflect a higher heart rate than the actual heart rate. Patient motion artifacts may also be present in signals sensed by implantable medical devices with intracardiac leads, such as when a unipolar electrode configuration involving a housing electrode is used for sensing, or whenever an electrode used for sensing is not in contact or in adequate contact with the heart.

SUMMARY

Techniques for determining whether artifacts are present in a cardiac electrogram are described. According to one example, a medical device senses a cardiac electrogram via electrodes. The medical device determines a derivative, e.g., a second order derivative, of the electrogram. The medical device detects beats within the derivative, e.g., by comparing a rectified version of the derivative to one or more thresholds determined based on a maximum of the rectified derivative.

The medical device determines whether the beats are periodic, and determines whether artifacts are present in the cardiac electrogram based on the determination of whether the beats are periodic. The medical device may determine whether the beats are periodic based, at least in part, on an analysis of beat to beat intervals. The medical device may further determine whether tachyarrhythmia is present and/or whether the cardiac rhythm of the patient is treatable based on the determination of whether the beats are periodic. For example, the medical device may determine that an electrogram is not treatable when the beats are periodic. Additionally, or alternatively, the medical device may determine whether to analyze a cardiac rhythm using the electrogram and/or store the electrogram based on the determination of whether artifacts are present.

In one example, the disclosure provides a method comprising determining a derivative of a cardiac electrogram of a patient, detecting beats within the derivative, determining whether the beats are periodic, and determining whether artifacts are present in the cardiac electrogram based on the determination of whether the beats are periodic.

In another example, the disclosure provides a system comprising a plurality of electrodes, a medical device coupled to the electrodes that senses a cardiac electrogram via the electrodes, and a processor. The processor determines a derivative of a cardiac electrogram of a patient, detects beats within the derivative, determines whether the beats are periodic, and determines whether artifacts are present in the cardiac electrogram based on the determination of whether the beats are periodic.

In another example, the disclosure provides a system comprising means for determining a derivative of a cardiac electrogram of a patient, means for detecting beats within the derivative, means for determining whether the beats are periodic, and means for determining whether artifacts are present in the cardiac electrogram based on the determination of whether the beats are periodic.

In another example, the disclosure provides a computer-readable medium comprising instructions that cause a programmable processor to determine a derivative of a cardiac electrogram of a patient, detect beats within the derivative, determine whether the beats are periodic, and determine whether artifacts are present in the cardiac electrogram based on the determination of whether the beats are periodic.

The details of one or more embodiments of the techniques of this disclosure are set forth in the accompanying drawings and the description below. Other features, objects, and advantages of the techniques of this disclosure will be apparent from the description and drawings, and from the claims.

DETAILED DESCRIPTION

Figure 1:
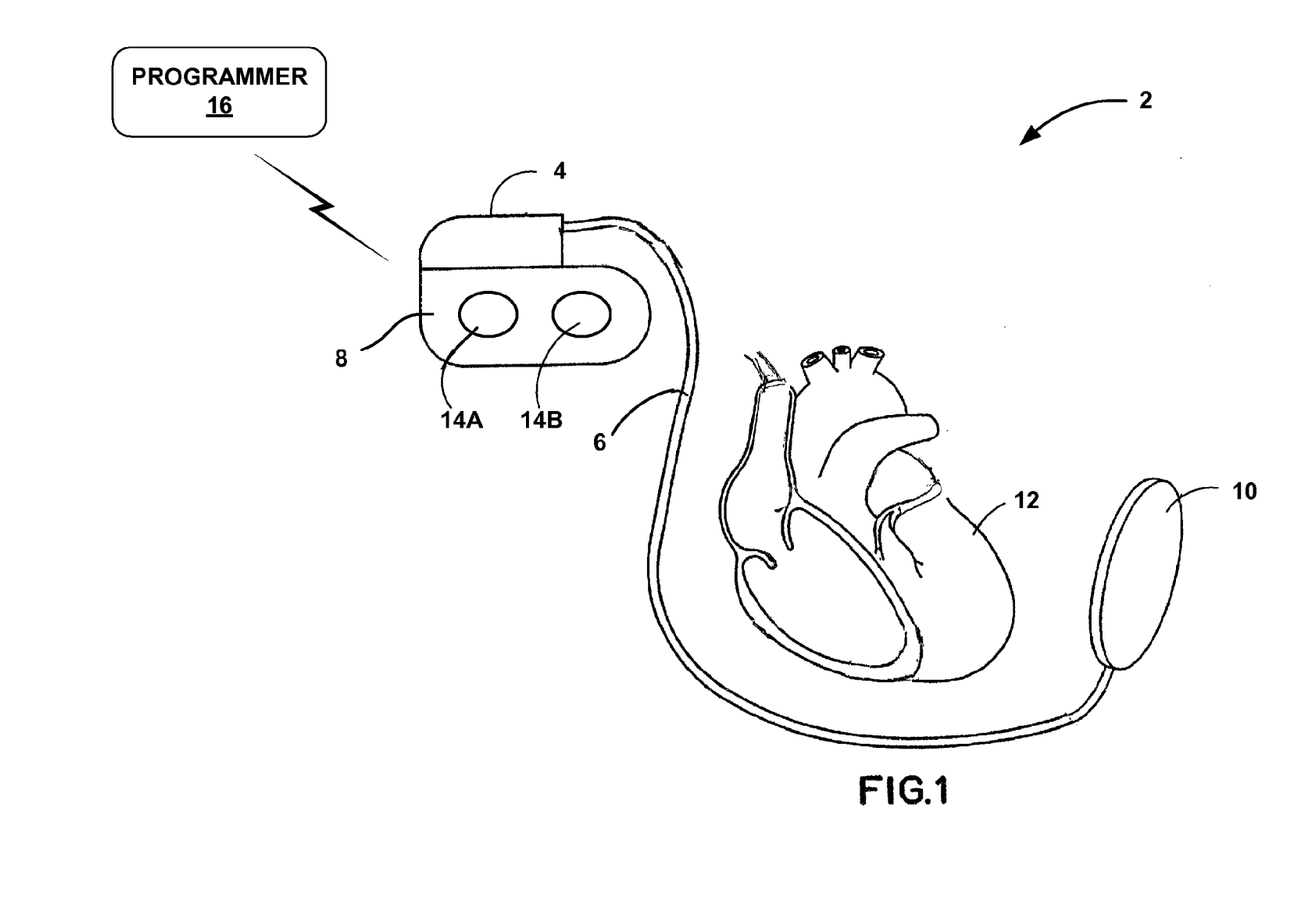
FIG. 1 is a conceptual diagram illustrating an example system that includes an implantable medical device in conjunction with the heart.

FIG. 1 is a conceptual diagram illustrating an example medical system 2 that includes an implantable medical device (IMD) 4 in conjunction with a heart 12 of a patient (not shown). IMD 4 may, for example, be a cardiac monitor, pacemaker, cardioverter, defibrillator, or any combination thereof.

IMD 4 may be a subcutaneously implantable medical device. In the illustrated example, IMD 4 is coupled to a subcutaneously implantable electrode 10 via an implantable lead 6. Subcutaneously implantable electrode may be, for example, a plate, patch or intramural electrode. In some examples, IMD 4 and electrode 10 may be implanted within a subcutaneous tissue layer of a patient, e.g., within the right chest, left chest, on the back, or any other suitable region within the patient.

In the illustrated example, IMD 4 includes a housing 8, with electrodes 14A and 14B on the housing ("housing electrodes 14"). Housing electrodes 14 may be formed integrally with an outer surface of hermetically-sealed housing 8 of IMD 16 or otherwise coupled to housing 8. In some examples, housing electrodes 14 are defined by an uninsulated portion of an outward facing portion of housing 8 of IMD 16. Other division between insulated and uninsulated portions of housing 8 may be employed to define two or more housing electrodes 14. In some examples, a housing electrode 14 comprises substantially all of housing 8.

As described in further detail with reference to FIG. 2, housing 8 may enclose a signal generator that generates therapeutic stimulation, such as cardiac pacing pulses and defibrillation shocks, as well as a sensing module for monitoring the rhythm of heart 12. IMD 4 may sense cardiac electrical signals, e.g., electrical signals attendant to the depolarization and repolarization of heart 12, via any combination of electrodes 10 and 14, and may deliver therapeutic stimulation, e.g., shocks, via any combination of electrodes 10 and 14. In some examples, IMD 4 does not provide therapy, and instead acts as a patient cardiac monitor, e.g., loop recorder.

The illustrated numbers and configurations of electrodes 10 and 14 and leads are merely examples. In some examples, a subcutaneously implantable IMD 4 is not coupled any lead, and senses cardiac signals and delivers therapeutic stimulation via housing electrodes 14. In some examples, IMD 4 is coupled to one or more transvenous leads, each lead including one or more electrodes for sensing and stimulation, or one or more epicardial leads. Furthermore, IMD 4 need not be subcutaneously implantable.

System 2 may also include a programmer 16, as illustrated in FIG. 1. In some examples, programmer 16 may be a handheld computing device, computer workstation, or networked computing device. Programmer 16 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 16 can additionally or alternatively include a peripheral pointing device, such as a mouse, via which a user may interact with the user interface. In some embodiments, a display of programmer 16 may include a touch screen display, and a user may interact with programmer 16 via the display. It should be noted that the user may also interact with programmer 16 and/or IMD 4 remotely via a networked computing device.

A user, such as a physician, technician, surgeon, electrophysiologist, or other clinician, may interact with programmer 16 to communicate with IMD 4. For example, the user may interact with programmer 16 to retrieve physiological or diagnostic information from IMD 4. A user may also interact with programmer 16 to program IMD 4, e.g., select values for operational parameters of the IMD.

For example, the user may use programmer 16 to retrieve information from IMD 4 regarding the rhythm of heart 12, trends therein over time, or tachyarrhythmic episodes. As another example, the user may use programmer 16 to retrieve information from IMD 4 regarding other sensed physiological parameters of the patient, such as intracardiac or intravascular pressure, activity, posture, respiration, or thoracic impedance. As another example, the user may use programmer 16 to retrieve information from IMD 4 regarding the performance or integrity of IMD 4 or other components of system 2, such as lead 6, or a power source of IMD 4. In some examples, this information may be presented to the user as an alert.

The user may use programmer 16 to program a therapy progression, select electrodes used to deliver defibrillation or cardioversion pulses, select waveforms for the defibrillation or cardioversion pulses, or select or configure a tachyarrhythmia detection algorithm for IMD 4. The user may also use programmer 16 to program aspects of other therapies provided by IMD 4, such as pacing therapies.

IMD 4 and programmer 16 may communicate via wireless communication using any techniques known in the art. Examples of communication techniques may include, for example, low frequency or radiofrequency (RF) telemetry, but other techniques are also contemplated. In some examples, programmer 16 may include a programming head that may be placed proximate to the patient's body near the IMD 4 implant site in order to improve the quality or security of communication between IMD 4 and programmer 16.

Figure 2:
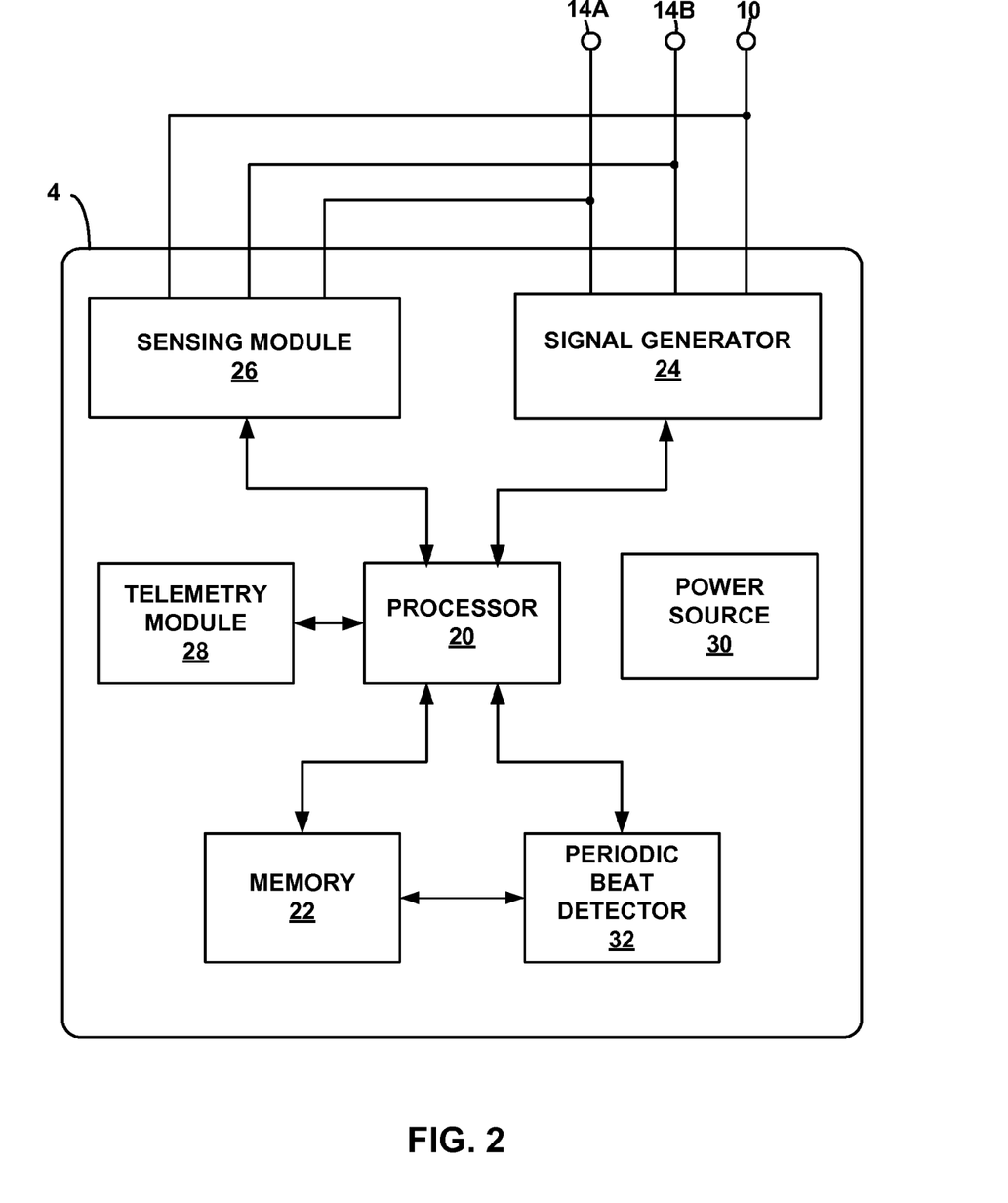
FIG. 2 is a block diagram illustrating an example configuration of the implantable medical device of FIG. 1.

FIG. 2 is a block diagram illustrating an example configuration of IMD 4. In the illustrated example, IMD 16 includes a processor 20, memory 22, signal generator 24, sensing module 26, telemetry module 28, power source 30 and periodic beat detector 32. Memory 22 includes computer-readable instructions that, when executed by processor 20, cause IMD 4 and processor 20 to perform various functions attributed to IMD 4 and processor 20 herein. Memory 22 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 20 may include any one or more of a microprocessor, a controller, a digital signal processor (DSP), an application specific integrated circuit (ASIC), a field-programmable gate array (FPGA), or equivalent discrete or analog logic circuitry. In some examples, processor 20 may include multiple components, such as any combination of one or more microprocessors, one or more controllers, one or more DSPs, one or more ASICs, or one or more FPGAs, as well as other discrete or integrated logic circuitry. The functions attributed to processor 20 herein may be embodied as software, firmware, hardware or any combination thereof.

Processor 20 may control signal generator 24 to deliver stimulation therapy to heart 12 according to a selected one or more of therapy programs or parameters, which may be stored in memory 22. Signal generator 24 is electrically coupled to electrodes 10 and 14. Signal generator 24 is configured to generate and deliver electrical stimulation therapy to heart 12. For example, signal generator 24 may deliver defibrillation or cardioversion shocks to heart 12 via at least two of electrodes 10 and 14. In some examples, signal generator 24 may deliver pacing pulses via at least two of electrodes 10 and 14. In some examples, signal generator 24 delivers pacing, cardioversion, or defibrillation stimulation in the form of electrical pulses. In other examples, signal generator may deliver one or more of these types of stimulation in the form of other signals, such as sine waves, square waves, or other substantially continuous time signals. Furthermore, in examples in which IMD 4 does not deliver stimulation therapy, the IMD need not include signal generator 24.

Signal generator 24 may include a switch module and processor 20 may use the switch module to select, e.g., via a data/address bus, which of the available electrodes are used to deliver defibrillation pulses or pacing pulses. The switch module may include a switch array, switch matrix, multiplexer, or any other type of switching device suitable to selectively couple stimulation energy to selected electrodes.

Electrical sensing module 26 monitors signals from any combination of electrodes 10 and 14. Sensing module 26 may also include a switch module to select which of the available electrodes are used to sense the heart activity, depending upon which electrode combination is used in the current sensing configuration. In some examples, processor 20 may select the electrodes that function as sense electrodes, i.e., select the sensing configuration, via the switch module within sensing module 26. Processor 20 may control the functionality of sensing module 26 by providing signals via a data/address bus. In some examples, housing electrodes 14 are used for cardiac sensing.

Sensing module 26 may include one or more detection channels, each of which may comprise an amplifier. The detection channels may be used to sense the cardiac signals. Some detection channels may detect events, such as R-waves, and provide indications of the occurrences of such events to processor 20. One or more other detection channels may provide the signals to an analog-to-digital converter, for processing or analysis by processor 20. In response to the signals from processor 20, the switch module within sensing module 26 may couple selected electrodes to selected detection channels.

For example, sensing module 26 may comprise one or more narrow band channels, each of which may include a narrow band filtered sense-amplifier that compares the detected signal to a threshold. If the filtered and amplified signal is greater than the threshold, the narrow band channel indicates that a certain electrical cardiac event, e.g., depolarization, has occurred. Processor 20 then uses that detection in measuring frequencies of the sensed events.

In one example, at least one narrow band channel may include an R-wave amplifier. In some examples, the R-wave amplifiers may take the form of an automatic gain controlled amplifier that provides an adjustable sensing threshold as a function of the measured R-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety.

In some examples, sensing module 26 includes a wide band channel which may comprise an amplifier with a relatively wider pass band than the R-wave amplifier. Signals from the selected sensing electrodes that are selected for coupling to this wide-band amplifier may be converted to multi-bit digital signals by an analog-to-digital converter (ADC) provided by, for example, sensing module 26 or processor 20. In some examples, processor 20 may store signals the digitized versions of signals from the wide band channel in memory 22 as electrograms (EGMs). The EGMs may be obtained from within a patient, e.g., as with an intra electrocardiogram or a subcutaneous electrocardiogram, or from a surface of the patient, e.g., as with a surface electrocardiogram. In this manner, the EGMs may be obtained in any manner. Additionally, EGMs, as used, herein may include electrocardiograms (ECGs or EKGs), electroencephalograms (EEGs), or other type of electrograms. In some examples, the storage of such EGMs in memory 22 may be under the control of a direct memory access circuit.

In some examples, processor 20 may employ digital signal analysis techniques to characterize the digitized signals from the wide band channel to, for example detect and classify the patient's heart rhythm. Processor 20 may detect and classify the patient's heart rhythm by employing any of the numerous signal processing methodologies known in the art.

If IMD 4 is configured to generate and deliver pacing pulses to heart 12, processor 20 may maintain escape interval counters that may be reset upon sensing of R-waves by sensing module 26. Signal generator 24 may include pacer output circuits that are coupled, e.g., selectively by a switching module, to any combination of electrodes 10 and 14 appropriate for delivery of a pacing pulse to heart 12. Processor 20 may reset the escape interval counters upon the generation of pacing pulses by signal generator 24, and thereby control the basic timing of cardiac pacing functions, including anti-tachyarrhythmia pacing (ATP).

The value of the count present in the escape interval counters when reset by sensed depolarizations may be used by processor 20 to measure the durations of R-R intervals, which are measurements that may be stored in memory 22. Processor 20 may use the count in the interval counters to detect a tachyarrhythmia, such as ventricular fibrillation or ventricular tachycardia. A portion of memory 22 may be configured as a plurality of recirculating buffers, capable of holding series of measured intervals, which may be analyzed by processor 20 to determine whether the patient's heart 12 is presently exhibiting atrial or ventricular tachyarrhythmia.

In some examples, an arrhythmia detection method may include any suitable tachyarrhythmia detection algorithms. In one example, processor 20 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. is incorporated herein by reference in their entireties. However, other arrhythmia detection methodologies may also be employed by processor 30 in other examples.

In some examples, processor 20 may determine that tachyarrhythmia has occurred by identification of shortened R-R interval lengths. Generally, processor 20 detects tachycardia when the interval length falls below 360 milliseconds (ms) and fibrillation when the interval length falls below 320 ms. These interval lengths are merely examples, and a user may define the interval lengths as desired, which may then be stored within memory 22. This interval length may need to be detected for a certain number of consecutive cycles, for a certain percentage of cycles within a running window, or a running average for a certain number of cardiac cycles, as examples.

In the event that processor 20 detects a ventricular tachyarrhythmia based on signals from sensing module 26, processor 20 may control signal generator 24 to deliver an anti-tachyarrhythmia pacing regimen. If IMD 4 is configured to generate and deliver cardioversion or defibrillation pulses to heart 12, signal generator 24 may include a high voltage charge circuit and a high voltage output circuit. In response to the detection of atrial or ventricular fibrillation or tachycardia requiring a cardioversion or defibrillation pulse, processor 20 may initiate charging of the high voltage capacitors of the high voltage charge circuit of signal generator 24 and control delivery of a shock, pulse or other treatment by the signal generator.

Telemetry module 28 includes any suitable hardware, firmware, software or any combination thereof for communicating with another device, such as programmer 16 (FIG. 1). Under the control of processor 20, telemetry module 28 may receive downlink telemetry from and send uplink telemetry to programmer 16 with the aid of an antenna, which may be internal and/or external. In some examples, processor 20 may transmit cardiac signals, e.g., ECG signals, produced by sensing module 26 to programmer 16. Programmer 16 may interrogate IMD 4 to receive the cardiac signals. Processor 20 may store heart signals within memory 22, and retrieve stored heart signals from memory 22. Processor 20 may also generate and store marker codes indicative of different cardiac events that sensing module 26 detects, and transmit the marker codes to programmer 16. An example IMD with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety. Information which processor 20 may transmit to programmer 16 via telemetry module 28 may also include indications of tachyarrhythmia detection, subsequent determinations that the tachyarrhythmia was nontreatable, or subsequent indications of therapy delivery. Such information may be included as part of a marker channel with an EGM.

The various components of IMD 4 are coupled to power source 30, which may include a rechargeable or non-rechargeable battery. A non-rechargeable battery may be capable of holding a charge for several years, while a rechargeable battery may be inductively charged from an external device, e.g., on a daily or weekly basis.

As illustrated in FIG. 2, IMD 4 may also include a periodic beat detector 32. Periodic beat detector 32 may receive digitized EGMs from sensing module 26 and/or processor 20. Periodic beat detector 32 analyzes the EGM to determine whether artifacts, such as motion artifacts, are present in the EGM. More particularly, periodic beat detector 32 analyzes the EGM to determine whether periodic beats are present in the EGM, which may indicate that the other components of the EGM are artifacts. Based on the determination of whether there are artifacts, IMD 4 may analyze a cardiac rhythm using the EGM. Alternatively, or additionally, IMD 4 may store the EGM within a memory based on the determination of whether artifacts are present. In this manner, the techniques of this disclosure may be utilized within a monitoring device, a pacemaker or any other type of medical device.

In some examples, periodic beat detector 32 receives a digitized EGM sample of a predetermined length, e.g., three seconds, that has been classified as a treatable tachyarrhythmia according to other tachyarrhythmia detection techniques, such as rate or morphology based techniques. If periodic beat detector 32 determines that there are periodic beats in the EGM, periodic beat detector 32 may reclassify the EGM as nontreatable. Periodic beats in the EGM may correspond to cardiac depolarizations at sinus rhythm, and may indicate that other components of the EGM that resulted in the tachyarrhythmia detection according to the other detection techniques being artifacts. Thus, the periodic beat detector 32 may, in some examples, determine whether a tachyarrhythmia is present based on a determination of whether an EGM has periodic beats.

Although processor 20 and periodic beat detector 32 are illustrated as separate modules in FIG. 2, processor 20 and periodic beat detector 32 may be incorporated in a single processing unit. Periodic beat detector 32, and any of its components discussed in greater detail below, may be a component of or module executed by processor 20.

Furthermore, the components of and functionality provided by a periodic beat detector 32 are described herein with respect to examples in which periodic beat detector 32 is located within IMD 4. However, it is understood that any one or more periodic beat detectors 32 may be individually or collectively provided by any one or more devices, such as IMD 4 and programmer 16, to individually or collectively provide the functionality described herein. Programmer 16 may receive digitized EGM signals from IMD 4 in embodiments in which programmer 16 comprises a periodic beat detector.

Figure 3:
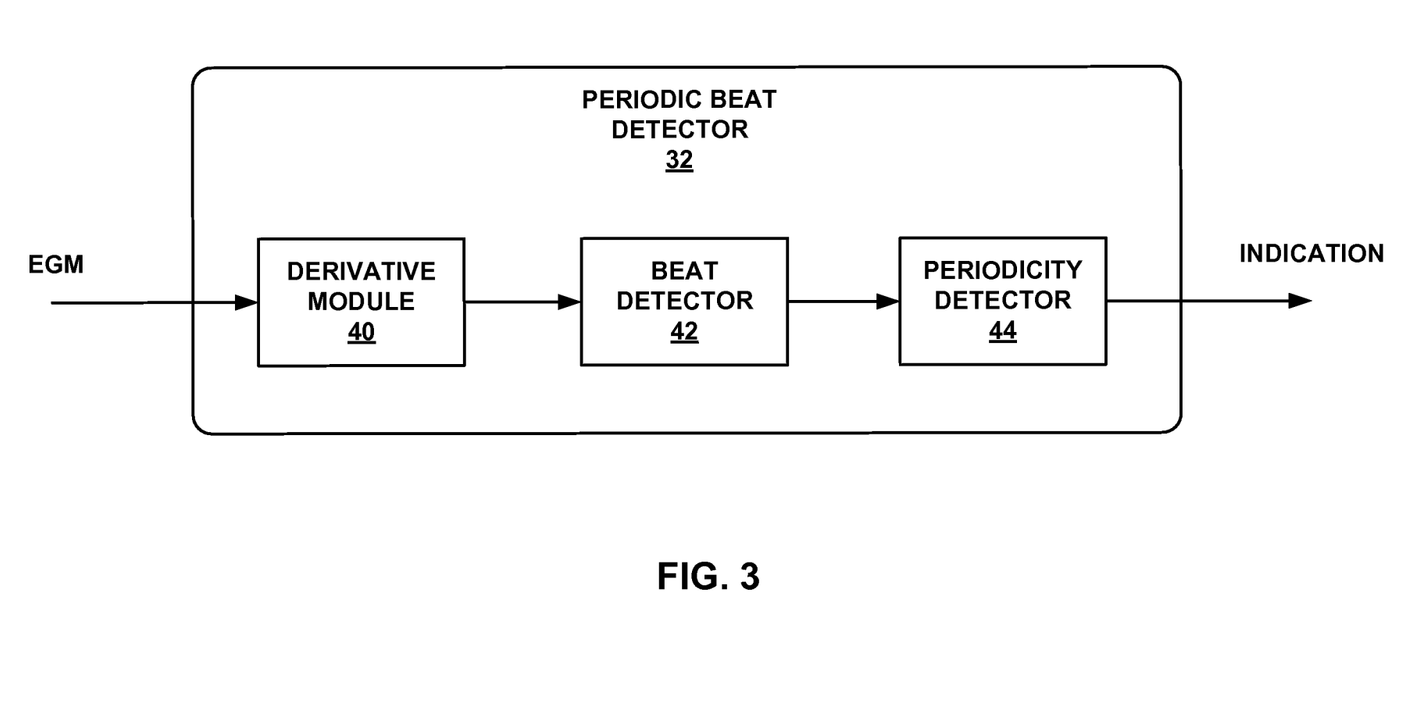
FIG. 3 is a block diagram illustrating an example configuration of a periodic beat detector.

FIG. 3 is a block diagram illustrating an example configuration of periodic beat detector 32. As illustrated in FIG. 3, periodic beat detector 32 may include a derivative module 40, beat detector 42, and periodicity detector 44.

Derivative module 40 receives a digitized EGM signal, which may be in the form of a sample with a predetermined length. Derivative module 40 determines a derivative of the signal. In some examples, derivative module 40 determines a second order derivative of the EGM. Derivative module 40 may determine a second order derivative by, for example, determining a second order sample-to-sample difference of the EGM, i.e., determining the differences between consecutive samples of the EGM, and then determining differences between consecutive ones of the differences.

Beat detector 42 receives the derivative of the EGM, and detects beats within the derivative. Beat detector 42 may rectify the derivative, and identify a maximum of the rectified derivative. Based on the maximum, beat detector 42 may determine a lower and higher threshold, which may be equal to 50% and 75% of the maximum according to one example. Beat detector 42 compares the rectified derivative of the EGM to the thresholds, and identifies beats in the rectified derivative of the EGM based on the comparisons.

Periodicity detector 44 analyzes the beats to determine whether they are periodic. Periodicity detector 44 may determine whether the beats are periodic based, at least in part, on an analysis of beat to beat intervals. Periodicity detector 44 may also identify a first beat and a last beat with the rectified derivative of the EGM sample, determine whether the beats are periodic based an analysis of a time within the predetermined sample length before the first beat and a time within the predetermined sample length after the last beat. Periodicity detector 44 may provide an indication of whether the beats are periodic, or whether the EGM is treatable, to processor 30. In other words, periodicity detector 44 may provide an indication that the cardiac rhythm represented by the EGM is treatable, e.g., via delivery of a shock, pulse or other treatments.

Figure 4:
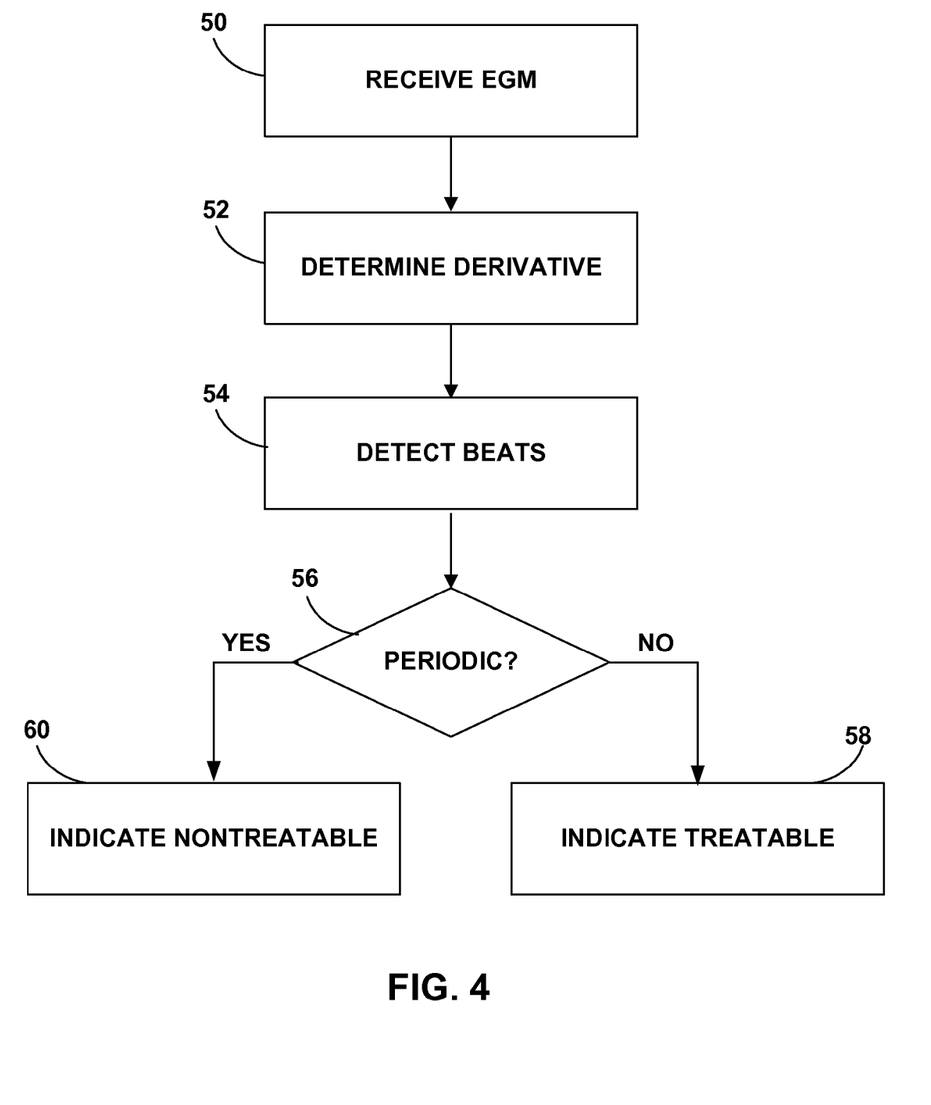
FIG. 4 is a flow diagram illustrating an example method for determining whether detected beats are periodic and indicating whether the cardiac rhythm is treatable.

FIG. 4 is a flow diagram illustrating an example method for determining whether detected beats are periodic and indicating whether the cardiac rhythm is treatable. The example method may be performed by any one or more processors described herein, or components thereof as described herein. The example method is described with respect to periodic beat detector 32 and its components.

According to the example method, periodic beat detector 32 receives an EGM, e.g., a sample of a predetermined length (50). Derivative module 40 determines a second-order derivative of the signal, e.g., a second order sample-to-sample difference of the EGM (52). Beat detector 42 detects beats within the derivative (54). Periodicity detector 44 analyzes the beats to determine whether they are periodic (56). If the beats are not periodic, periodicity detector 44 may indicate that the EGM, or the cardiac rhythm represented by the EGM, is treatable (58) or provide no indication as the EGM may have been previous classified as treatable. If the beats are periodic, periodicity detector 44 may indicate that the EGM is nontreatable (60).

Figure 5:
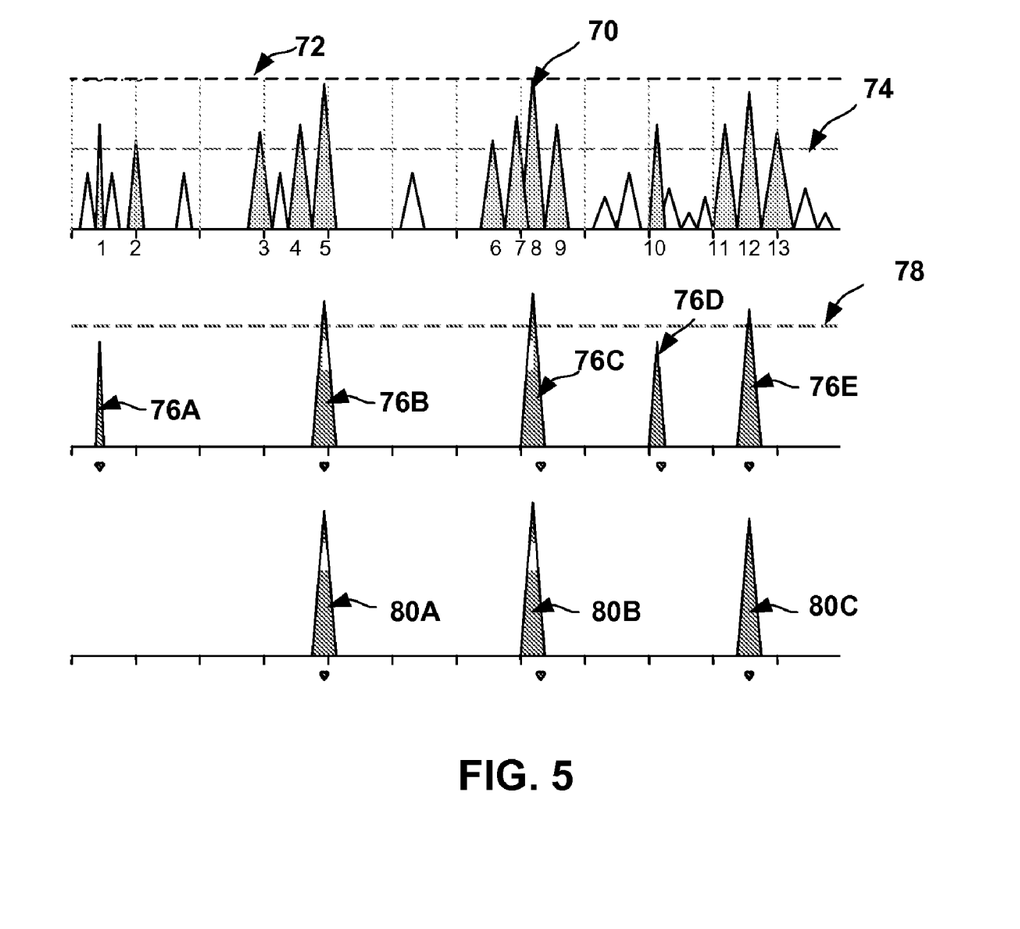
FIG. 5 is a diagram illustrating an example beat detection technique.

FIG. 5 is a diagram illustrating an example beat detection technique. The top graph illustrates a rectified, second order derivative of an EGM sample, which includes a plurality of pulses. For ease of illustration, only the maximum pulse 70 is labeled in FIG. 5. Based on the magnitude of maximum pulse 70, beat detector 44 may determine a maximum magnitude (72) of the derivative. Based on the maximum magnitude, beat detector 42 may determine a first, lower threshold 74, and a second, higher threshold 78. As discussed above, these thresholds may correspond to 50% and 75% of the maximum magnitude. Beat detector 42 may compare the pulses in the top graph to lower threshold 74 to detect the pulses that exceed threshold 74. Beat detector 42 may compare pulses that exceed threshold 74 to each other to identify which pulses qualify as small beats. In particular, beat detector 42 classifies pulses having a local maximum peak magnitude among the neighboring pulses within a window, e.g., 100 milliseconds (ms), before and after the pulse. In the illustrated example, beat detector 42 identifies small beats 76A-76E ("small beats 76"), as shown in the middle graph.

Beat detector 42 compares small beats 76 to the higher threshold 78. Beat detector 42 identifies which small beats 76 are large beats based on this comparison. In the illustrated example, beat detector 42 identifies large beats 80A-80C ("large beats 80"), as shown in the lower graph.

Figure 6:
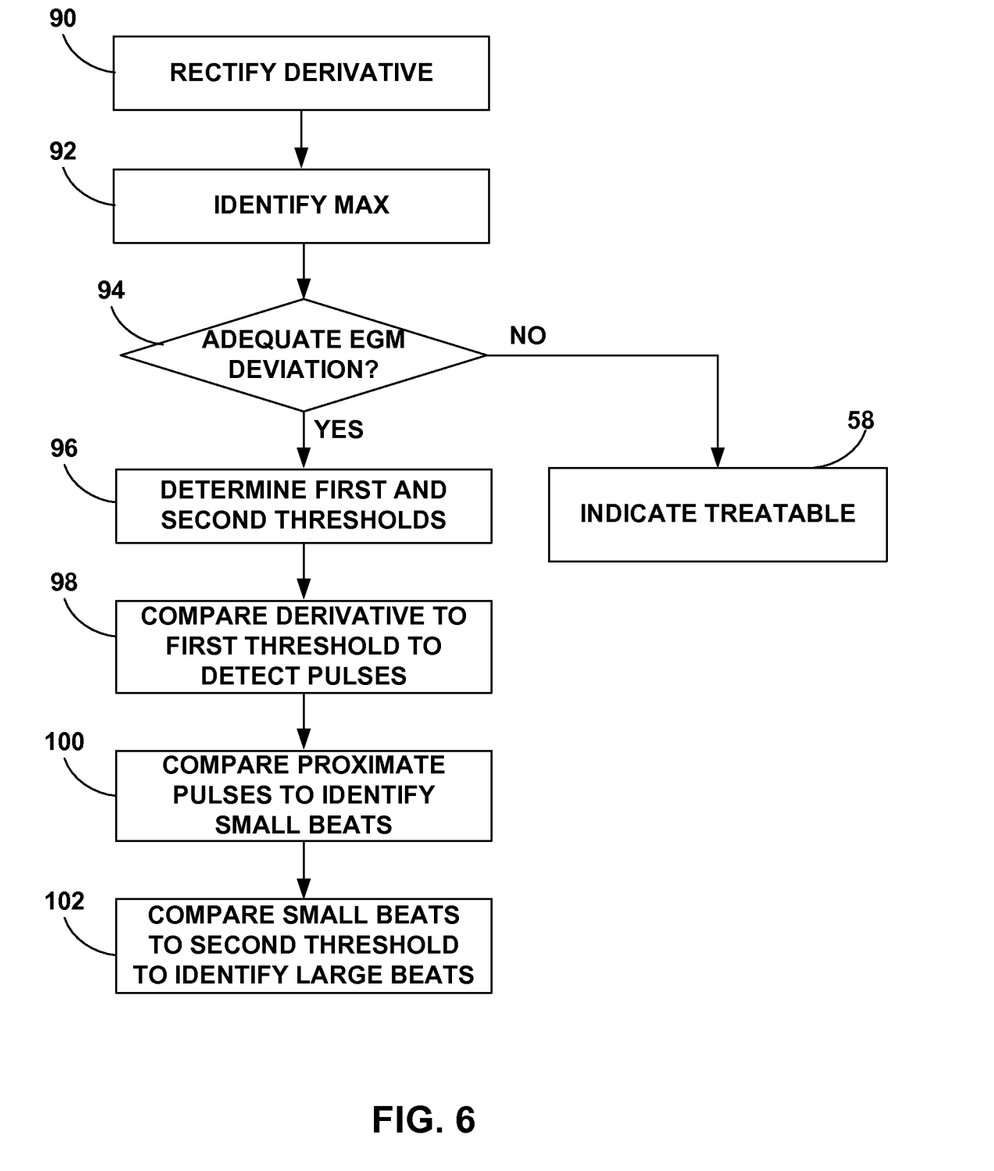
FIG. 6 is a flow diagram illustrating an example method for detecting beats based on a derivative of an electrogram.

FIG. 6 is a flow diagram illustrating an example method for detecting beats based on a derivative of an electrogram. The example method may be performed by any one or more processors described herein, or components thereof as described herein. The example method is described with respect to beat detector 42.

According to the example method, beat detector 42 rectifies the derivative of the EGM (90). Beat detector 42 then identifies a maximum of the rectified derivative (92). Beat detector 42 determines whether the EGM exhibits adequate deviation for further processing (94). For example, beat detector 42 may compare the magnitude of the rectified derivative of the EGM to a threshold. A magnitude below the threshold may indicate inadequate deviation of the EGM, which may be due to weakness of the signal. Accordingly, if beat detector 42 determines that the EGM deviation is inadequate, beat detector 42 (or periodicity module 44) may indicate that the EGM is treatable (58). In other words, beat detector 42 may indicate that the cardiac rhythm represented by the EGM is capable of treatment via defibrillation, cardioversion, ATP, or ATP delivered during charging.

If beat detector 42 determines that the EGM deviation is adequate, beat detector 42 may proceed to determine the first and second, e.g., lower and higher, threshold values (96). Beat detector 96 compares the derivative to the first threshold 74 to detect pulses (98). Beat detector 42 may then compare proximate pulses to identify small beats, e.g., local maximum pulses (100). Beat detector 42 compares the small beats to the second threshold 78 to identify large beats (102).

Figure 7:
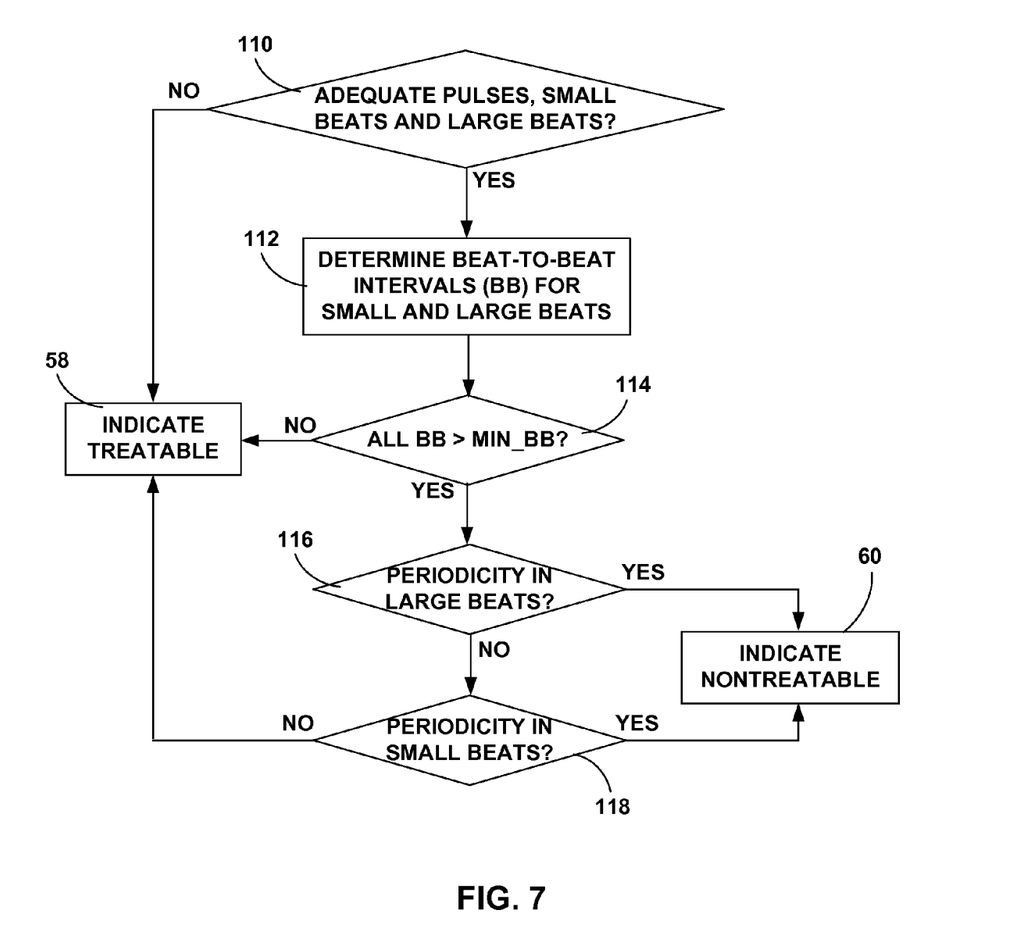
FIG. 7 is a flow diagram illustrating an example technique for indicating whether the cardiac rhythm is treatable based, in part, on whether detected beats are periodic.

FIG. 7 is a flow diagram illustrating an example technique for indicating whether the cardiac rhythm is treatable based, in part, on whether detected beats are periodic. The example method may be performed by any one or more processors described herein, or components thereof as described herein. The example method is described with respect to periodicity detector 44.

According to the example method, periodicity detector 44 determines whether there are adequate pulses, small beats, and large beats for further analysis (110). For example, periodicity detector 44 may compare the number of pulses, small beats and large beats to respective thresholds or the same threshold, such as at least three pulses, at least three small beats, and at least three large beats. An inadequate number of pulses, small beats, or large beats in a sample of a predetermined length may indicate a lack of periodicity. Another condition that may indicate inadequate large beats and lack of periodicity is a comparison of the number of small beats to the number of large beats. For example, if periodicity detector 44 determines that the number of large beats is the same as the number of small beats, periodicity detector may determine that there is an inadequate number of large beats. If periodicity detector 44 determines that there are inadequate pulses or beats, periodicity detector 44 may indicate that the EGM is treatable (58). As such, periodicity detector 44 may indicate that the EGM, or the cardiac rhythm represented by the EGM, is capable of being treated via defibrillation, cardioversion, ATP, or ATP delivered during charging.

Although illustrated as a single step performed by periodicity detector 44, the determinations of adequate pulses, small beats, and large beats may be performed as separate steps. For example, the determination of whether the sample includes adequate pulses may be made after rectifying the samples, and prior to identifying small beats, in which case a determination of inadequate pulses may result in indicating the EGM is treatable and not identifying small beats or large beats. The determinations of adequate small and large beats may similarly be performed after identification of the small and large beats, respectively. In such examples, these determinations may be made by beat detector 42, instead of periodicity detector 44.

If there are adequate pulses and beats, periodicity detector 44 determines beat-to-beat intervals for the small and large beats (112). Periodicity detector 44 compares the beat-to-beat intervals to a minimum beat-to-beat interval, which may be associated with a tachyarrhythmia detection rate or period, e.g., 170 beats per minute (114). Beat-to-beat intervals less than the minimum interval may indicate that, to the extent the beats are periodic and associated with cardiac activity, they indicate a treatable tachyarrhythmia. Accordingly, if any beat-to-beat interval is less than the minimum interval, periodicity detector 44 may indicate that the EGM is treatable (58).

If all beat-to-beat intervals are greater than the minimum interval, periodicity detector 44 determines whether there is periodicity in the large beats (116). If there is periodicity in the large beats, periodicity detector 44 indicates that the EGM is not treatable (60). If there is not periodicity in the large beats, periodicity detector 44 determines whether there is periodicity in the small beats (118). If there is periodicity in the small beats, periodicity detector 44 indicates that the EGM is not treatable (60). If there is not periodicity in the small beats, periodicity detector 44 indicates that the EGM is treatable (58).

The illustrated order of steps is merely an example. In other examples, the determination of beat-to-beat intervals (112), comparison to the minimum threshold (114) and determination of periodicity (116, 118) may all be performed for large beats prior to their performance with respect to small beats. Furthermore, these steps may not need to be performed for small beat in situations in which the numbers of large and small beats are the same.

Figure 8:
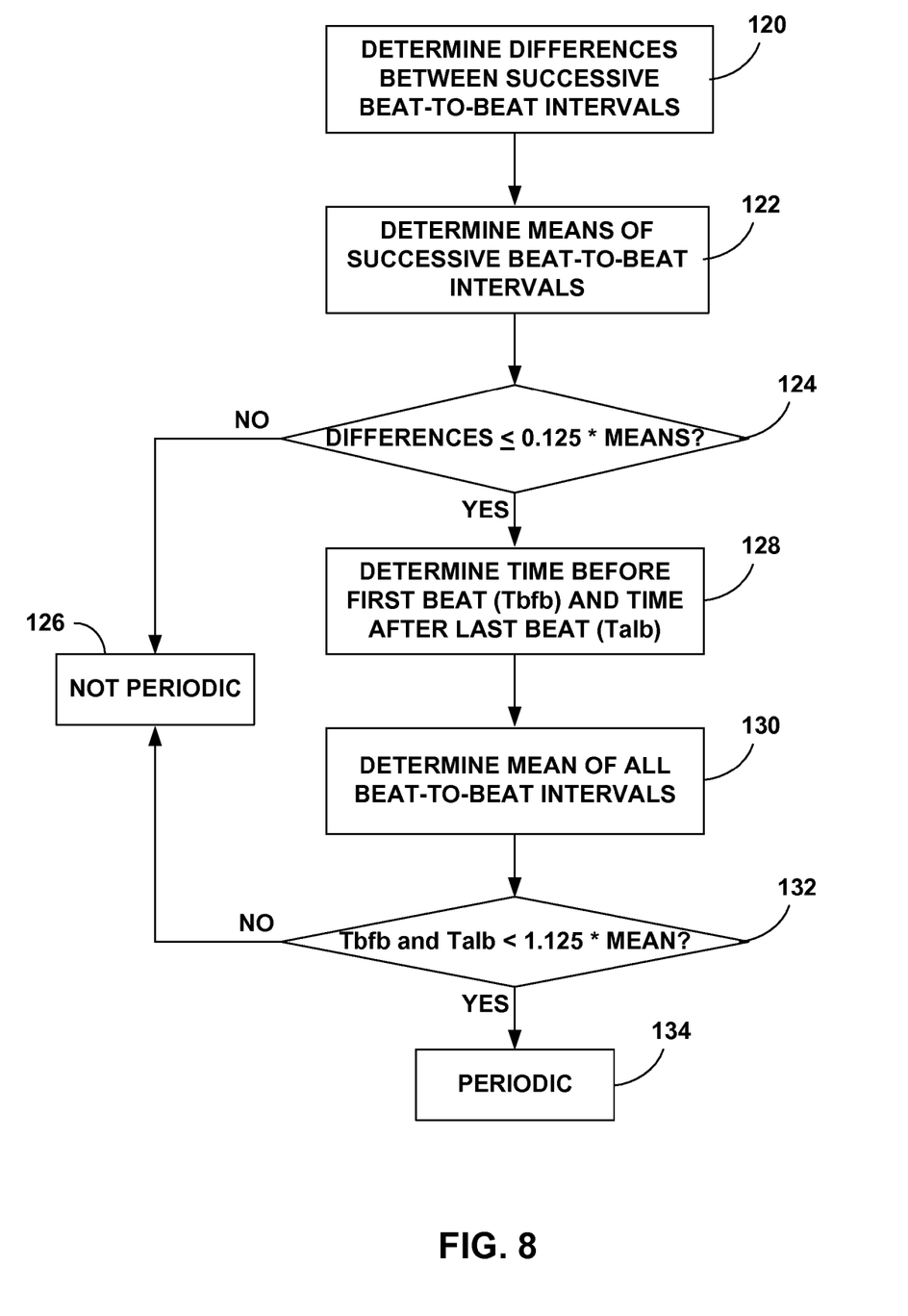
FIG. 8 is a flow diagram illustrating an example technique for determining whether detected beats are periodic.

FIG. 8 is a flow diagram illustrating an example technique for determining whether detected beats are periodic. The example method may be performed by any one or more processors described herein, or components thereof as described herein. The example method is described with respect to periodicity detector 44.

According to the illustrated example, periodicity detector 44 determines differences between successive beat-to-beat intervals (120), and also determines the means of successive beat-to-beat intervals (122). Periodicity detector 44 then compares the differences to the respective means to determine the relative size of the differences, e.g., the variability of the differences (124). In the illustrated example, periodicity detector 44 determines whether the differences exceed a fraction of the respective means, e.g., 0.125 * the means.

If the differences exceed the fraction of the respective means, periodicity detector 44 indicates that the EGM is not periodic (126). However, if the differences do not exceed the fraction of the respective means, periodicity detector 44 proceeds to determine the time before the first beat and the time after the last beat in the sample of predetermined length (128). Periodicity detector 44 also determines the means of all of the determined beat-to-beat intervals (130). Periodicity detector 44 compares the time before the first beat and the time after the last beat to the mean (132). For example, periodicity detector 44 may compare the time before the first beat and the time after the last beat to 1.125 * the mean, as illustrated in FIG. 8. If the time before the first beat or the time after the last beat exceeds the mean beat-to-beat interval by a significant, e.g., threshold, amount, this indicates lack of periodicity in the beats because another beat should have been present prior to the first beat or after the least beat. If the time before the first beat or the time after the last beat exceeds the mean beat-to-beat interval by a significant, e.g., threshold, amount, periodicity detector 44 indicates that the EGM is not periodic (126). If the time before the first beat or the time after the last beat does not exceed the mean beat-to-beat interval by a significant, e.g., threshold, amount, periodicity detector 44 indicates that the EGM is periodic (134).

Figure 9:
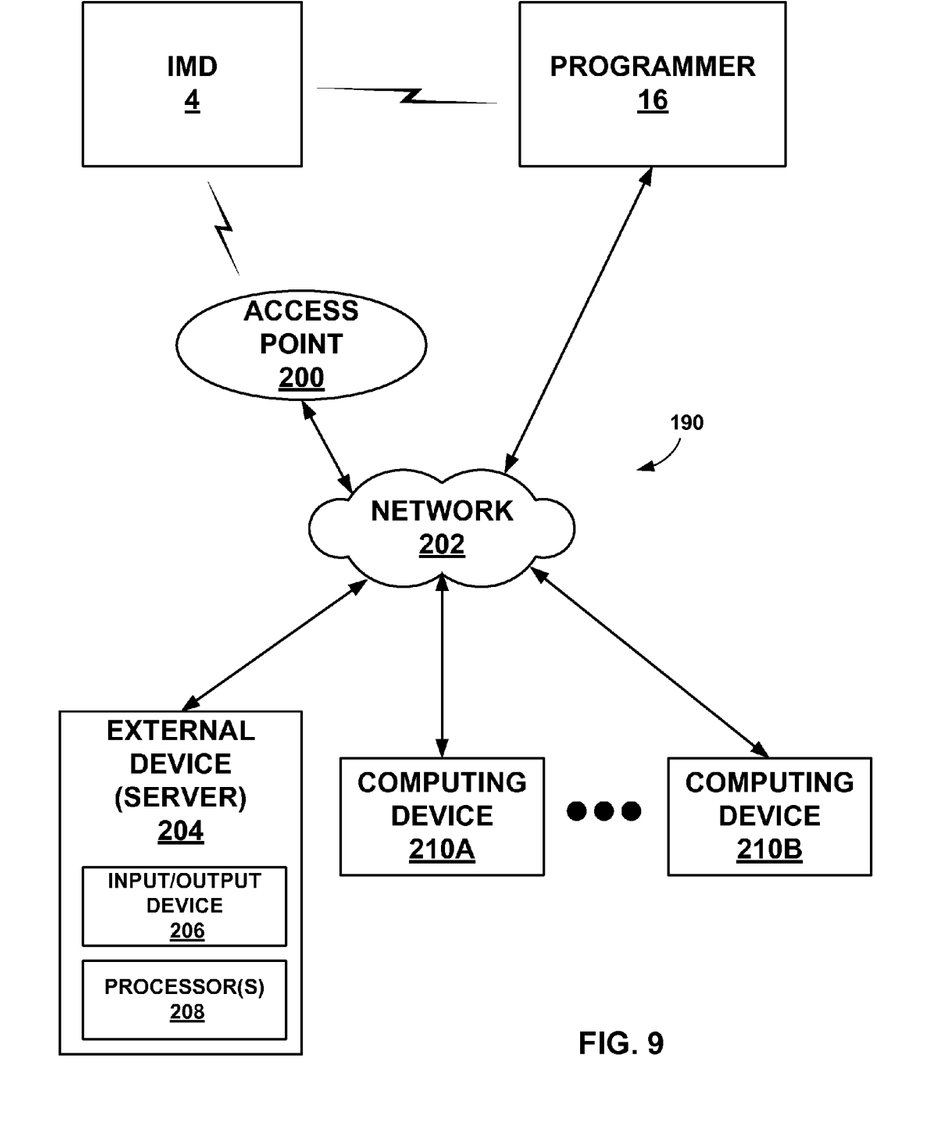
FIG. 9 is a block diagram illustrating an example system that includes an external device, such as a server, and one or more computing devices that are coupled to the IMD and programmer shown in FIG. 1 via a network.

FIG. 9 is a block diagram illustrating an example system 190 that includes an external device, such as a server 204, and one or more computing devices 210A-210N, that are coupled to the IMD 4 and programmer 16 shown in FIG. 1 via a network 202. In this example, IMD 4 may use its telemetry module 28 to communicate with programmer 16 via a first wireless connection, and to communication with an access point 200 via a second wireless connection. In the example of FIG. 9, access point 200, programmer 16, server 204, and computing devices 210A-210N are interconnected, and able to communicate with each other, through network 202. In some cases, one or more of access point 200, programmer 16, server 204, and computing devices 210A-210N may be coupled to network 202 through one or more wireless connections. IMD 4, programmer 16, server 204, and computing devices 210A-210N may each comprise one or more processors, such as one or more microprocessors, DSPs, ASICs, FPGAs, programmable logic circuitry, or the like, that may perform various functions and operations, such as those described herein. Network 202 may comprise a local area network, wide area network, or global network, such as the Internet. System 190 may be implemented, in some aspects, with general network technology and functionality similar to that provided by the Medtronic CareLink® Network developed by Medtronic, Inc., of Minneapolis, Minn.

Access point 200 may comprise a device that connects to network 202 via any of a variety of connections, such as telephone dial-up, digital subscriber line (DSL), or cable modem connections. In other embodiments, access point 200 may be coupled to network 202 through different forms of connections, including wired or wireless connections. In some embodiments, access point 200 may be co-located with a patient and may comprise one or more programming units and/or computing devices (e.g., one or more monitoring units) that may perform various functions and operations described herein. For example, access point 200 may include a home-monitoring unit that is co-located with the patient and that may monitor the activity of IMD 4.

In some examples, access point 200, server 204 or computing devices 210 may perform any of the various functions or operations described herein with respect to IMD 4 or programmer 16. For example, such devices may receive digitized EGM signals from IMD 4, and include a periodic beat detector 32 for analysis of the EGMS according to any of the techniques described herein.

Various examples have been described. These and other examples are within the scope of the following claims. For example, the techniques disclosed in this disclosure may be implemented by an implantable medical device that does not provide tachyarrhythmia therapies, such as an implantable monitoring device, an implantable pacemaker, or the like. Moreover, although described primarily with reference to implantable medical devices, the techniques disclosed herein may be implemented by an external medical device, such as an external defibrillator, e.g., to improve tachyarrhythmia detection, or to detect artifacts due to external electrode contact or patient motion. Furthermore, although described as indicating periodicity or treatability for a single sample, or based on a signal sample, other examples may consider a plurality of EGM samples. Some examples may indicate periodicity or treatability if X of the last Y, or Z consecutive samples are indicated to be periodic or treatable in the manner described herein.

The techniques described in this disclosure, including those attributed to IMD 4, programmer 16, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

The invention claimed is:

1. A method comprising:
    determining, using a processor, a derivative of a cardiac electrogram of a patient;
    detecting, using the processor, beats within the derivative;
    determining, using the processor, whether the beats are periodic; and
    determining, using the processor, whether artifacts are present in the cardiac electrogram based on the determination of whether the beats are periodic, wherein determining whether artifacts are present comprises determining whether a tachyarrhythmia is present in the patient based on the determination of whether the beats are periodic, and further comprising classifying the cardiac electrogram as treatable using a tachyarrhythmia detection technique, wherein determining whether a tachyarrhythmia is present comprises reclassifying the treatable cardiac electrogram as nontreatable when the beats are periodic.

2. The method of claim 1, wherein determining a derivative comprises determining a second order derivative.

3. A method comprising:
    determining, using a processor, a derivative of a cardiac electrogram of a patient;
    detecting, using the processor, beats within the derivative;
    determining, using the processor, whether the beats are periodic; and
    determining, using the processor, whether artifacts are present in the cardiac electrogram based on the determination of whether the beats are periodic, wherein detecting beats comprises:
    comparing the derivative to a first threshold to detect small beats; and
    comparing the derivative to a second threshold to detect large beats,
    wherein the first threshold is smaller than the second threshold.

4. The method of claim 3, further comprising:
    rectifying the derivative;
    identifying a maximum of the derivative; and
    determining the first threshold and the second threshold based on the maximum,
    wherein comparing the derivative to the first and second thresholds comprises comparing the rectified derivative to the first and second thresholds.

5. The method of claim 3, wherein determining whether the beats are periodic comprises:
    determining whether the large beats are periodic;
    determining whether the small beats are periodic if the large beats are not periodic; and
    determining that the beats are periodic if either the large or small beats are periodic.

6. The method of claim 1, wherein determining whether the beats are periodic comprises determining beat to beat intervals between successive beats.

7. The method of claim 6, wherein determining whether the beats are periodic comprises:
    comparing the beat to beat intervals to a minimum beat to beat interval threshold; and
    determining that beats are not periodic if any of the beat to beat intervals is less than the threshold.

8. A method comprising:
    determining, using a processor, a derivative of a cardiac electrogram of a patient;
    detecting, using the processor, beats within the derivative;
    determining, using the processor, whether the beats are periodic; and
    determining, using the processor, whether artifacts are present in the cardiac electrogram based on the determination of whether the beats are periodic, wherein determining whether the beats are periodic comprises determining beat to beat intervals between successive beats, and wherein determining whether the beats are periodic comprises:
    determining differences between successive beat to beat intervals;
    determining means of successive beat to beat intervals;
    comparing the differences to the means; and
    determining whether the beats are periodic based on the comparison.

9. A method comprising:
    determining, using a processor, a derivative of a cardiac electrogram of a patient;
    detecting, using the processor, beats within the derivative;
    determining, using the processor, whether the beats are periodic; and determining, using the processor, whether artifacts are present in the cardiac electrogram based on the determination of whether the beats are periodic, wherein determining whether the beats are periodic comprises determining beat to beat intervals between successive beats, and wherein the cardiac electrogram comprises a sample of a predetermined length of time, the method further comprising:

determining a time before a first one of the beats;
determining a time after a last one of the beats;
determining a mean of the beat to beat intervals;
comparing the time before a first one of the beats and the time after a last one of the beats to the mean; and
determining whether the beats are periodic based on the comparisons.

10. A method comprising:
determining, using a processor, a derivative of a cardiac electrogram of a patient;
detecting, using the processor, beats within the derivative;
determining, using the processor, whether the beats are periodic; and
determining, using the processor, whether artifacts are present in the cardiac electrogram based on the determination of whether the beats are periodic, wherein determining whether the beats are periodic comprises:
determining a number of the beats;
comparing the number to a threshold; and
determining whether the beats are periodic based on the comparison.

11. The method of claim 1, further comprising determining whether to analyze a cardiac rhythm using the electrogram based on the determination of whether artifacts are present.

12. The method of claim 1, further comprising determining whether to store the electrogram within a memory based on the determination of whether artifacts are present.

13. A system comprising:
a plurality of electrodes;
a medical device coupled to the electrodes that senses a cardiac electrogram via the electrodes; and
a processor that:
determines a derivative of a cardiac electrogram of a patient,
detects beats within the derivative,
determines whether the beats are periodic, and
determines whether artifacts are present in the cardiac electrogram based on the determination of whether the beats are periodic, wherein the processor compares the derivative to a first threshold to detect small beats, and compares the derivative to a second threshold to detect large beats, and
wherein the first threshold is smaller than the second threshold.

14. The system of claim 13, wherein the processor determines whether a tachyarrhythmia is present in the patient based on the determination of whether the beats are periodic.

15. The system of claim 14, wherein the processor classifies the cardiac electrogram as treatable using a tachyarrhythmia detection technique, and wherein the processor reclassifies the treatable cardiac electrogram as nontreatable when the beats are periodic.

16. The system of claim 13, the derivative comprises a second order derivative.

17. The system of claim 13, wherein the processor:
rectifies the derivative,
identifies a maximum of the derivative,
determines the first threshold and the second threshold based on the maximum, and
compares the rectified derivative to the first and second thresholds.

18. The system of claim 13, wherein the processor:
determines whether the large beats are periodic,
determines whether the small beats are periodic if the large beats are not periodic, and
determines that the beats are periodic if either the large or small beats are periodic.

19. The system of claim 13, wherein the processor determines beat to beat intervals between successive beats and determines whether the beats are periodic based on the beat to beat intervals.

20. The system of claim 19, wherein the processor compares the beat to beat intervals to a minimum beat to beat interval threshold, and determines that beats are not periodic if any of the beat to beat intervals is less than the threshold.

21. A system comprising:
a plurality of electrodes;
a medical device coupled to the electrodes that senses a cardiac electrogram via the electrodes; and
a processor that:
determines a derivative of a cardiac electrogram of a patient,
detects beats within the derivative,
determines whether the beats are periodic, and
determines whether artifacts are present in the cardiac electrogram based on the determination of whether the beats are periodic, wherein the processor determines beat to beat intervals between successive beats and determines whether the beats are periodic based on the beat to beat intervals, and wherein the processor:
determines differences between successive beat to beat intervals,
determines means of successive beat to beat intervals,
compares the differences to the means, and
determines whether the beats are periodic based on the comparison.

22. A system comprising:
a plurality of electrodes;
a medical device coupled to the electrodes that senses a cardiac electrogram via the electrodes; and
a processor that:
determines a derivative of a cardiac electrogram of a patient,
detects beats within the derivative,
determines whether the beats are periodic, and
determines whether artifacts are present in the cardiac electrogram based on the determination of whether the beats are periodic, wherein the processor determines beat to beat intervals between successive beats and determines whether the beats are periodic based on the beat to beat intervals, and wherein the cardiac electrogram comprises a sample of a predetermined length of time, and the processor:
determines a time before a first one of the beats,
determines a time after a last one of the beats,
determines a mean of the beat to beat intervals,
compares the time before a first one of the beats and the time after a last one of the beats to the mean, and
determines whether the beats are periodic based on the comparisons.

23. A system comprising:
a plurality of electrodes;
a medical device coupled to the electrodes that senses a cardiac electrogram via the electrodes; and a processor that:
  determines a derivative of a cardiac electrogram of a patient,
  detects beats within the derivative,
  determines whether the beats are periodic, and
  determines whether artifacts are present in the cardiac electrogram based on the determination of whether the beats are periodic, wherein the processor:
  determines a number of the beats,
  compares the number to a threshold, and
  determines whether the beats are periodic based on the comparison.

24. The system of claim 13, wherein the processor comprises a processor of the medical device.

25. A system comprising:
  a plurality of electrodes;
  a medical device coupled to the electrodes that senses a cardiac electrogram via the electrodes; and
  a processor that:
    determines a derivative of a cardiac electrogram of a patient,
    detects beats within the derivative,
    determines whether the beats are periodic, and
    determines whether artifacts are present in the cardiac electrogram based on the determination of whether the beats are periodic, wherein the electrodes comprise implantable electrodes and the medical device comprises an implantable medical device.

26. The system of claim 25, wherein the implantable medical device comprises a subcutaneously implantable medical device comprising a housing, and the electrodes comprise electrodes on or integral with the housing.

27. The system of claim 13, wherein the processor determines whether to analyze a cardiac rhythm using the electrogram based on the determination of whether artifacts are present.

28. The system of claim 13, further comprising a memory, wherein the processor determines whether to store the electrogram within the memory based on the determination of whether artifacts are present.

29. A system comprising:
  means for determining a derivative of a cardiac electrogram of a patient;
  means for detecting beats within the derivative;
  means for determining whether the beats are periodic; and
  means for determining whether artifacts are present in the cardiac electrogram based on the determination of whether the beats are periodic, wherein means for determining whether artifacts are present comprises means for determining whether a tachyarrhythmia is present in the patient based on the determination of whether the beats are periodic, and further comprising means for classifying the cardiac electrogram as treatable using a tachyarrhythmia detection technique, wherein means for determining whether a tachyarrhythmia is present comprises means for reclassifying the treatable cardiac electrogram as nontreatable when the beats are periodic.

30. A computer-readable storage medium comprising instructions that cause a programmable processor to:
  determine a derivative of a cardiac electrogram of a patient;
  detect beats within the derivative;
  determine whether the beats are periodic; and
  determine whether artifacts are present in the cardiac electrogram based on the determination of whether the beats are periodic, wherein determining whether artifacts are present comprises determining whether a tachyarrhythmia is present in the patient based on the determination of whether the beats are periodic, and further comprising classifying the cardiac electrogram as treatable using a tachyarrhythmia detection technique, wherein determining whether a tachyarrhythmia is present comprises reclassifying the treatable cardiac electrogram as nontreatable when the beats are periodic.

* * * * *